United States Patent [19]

Holyoke, Jr.

[11] 4,316,911

[45] Feb. 23, 1982

[54] UREIDOSULFENYL CARBAMATE NEMATICIDES

[75] Inventor: Caleb W. Holyoke, Jr., Newark, Del.

[73] Assignee: E. I. Du Pont de Nemours and Company, Wilmington, Del.

[21] Appl. No.: 203,635

[22] Filed: Nov. 3, 1980

[51] Int. Cl.$^3$ .................... A01N 37/18; C07C 119/18
[52] U.S. Cl. .................................. 424/298; 260/453.3
[58] Field of Search .......................... 260/453.1, 453.3; 424/298

[56] References Cited

U.S. PATENT DOCUMENTS

| 3,530,220 | 9/1970 | Buchanan | 260/453.3 |
| 3,658,870 | 4/1972 | Buchanan | 260/453.3 |
| 3,763,143 | 10/1973 | Buchanan | 260/453.3 |

FOREIGN PATENT DOCUMENTS

| 848911 | 5/1977 | Belgium | 260/453.3 |
| 855928 | 12/1977 | Belgium | 260/453.3 |
| 2654246 | 6/1977 | Fed. Rep. of Germany | 260/453.3 |
| 2828133 | 1/1980 | Fed. Rep. of Germany | 260/453.3 |
| 2934729 | 3/1980 | Fed. Rep. of Germany | 260/453.3 |

OTHER PUBLICATIONS

EP 5,249, Bayer Application of May 10, 1978.
EP 5,780, Bayer Application of Jun. 3, 1978.

*Primary Examiner*—John M. Ford
*Assistant Examiner*—Robert C. Whittenbaugh

[57] ABSTRACT

Plant parasitic nematodes are controlled by ureidosulfenyl carbamates such as 2-(dimethylamino)-N-[[N-methyl-N-[N-methyl-N-(2-propynylaminocarbonyl)aminothio]aminocarbonyloxy]]-2-oxoethanimidothioic acid, methyl ester.

24 Claims, No Drawings

UREIDOSULFENYL CARBAMATE NEMATICIDES

BACKGROUND OF THE INVENTION

This invention relates to ureidosulfenyl carbamate derivatives, and, more particularly, to unsaturated examples thereof, and their use in controlling nematodes.

German Pat. DT No. 2,934,729 discloses and claims trialkylurea sulfenyl carbamates of the formula $$\begin{array}{c} R_1 \\ \diagdown \\ N-C-N-S-N-C-O-N=C \\ \diagup \quad \| \quad | \quad | \quad \| \quad \diagdown \\ R_2 \quad O \; R_3 \; CH_3 \; O \quad \quad R_5 \end{array} \begin{array}{c} SR_4 \end{array}$$

wherein
$R_1$ and $R_2$ can be $C_1$–$C_4$ alkyl or $C_3$–$C_6$ cycloalkyl;
$R_3$ can be $C_1$–$C_8$ alkyl or $C_3$–$C_6$ cycloalkyl;
$R_4$ can be $C_1$–$C_3$ alkyl or allyl; and
$R_5$ can be $CH_3$ or a group of the formula $$\begin{array}{c} R_6 \\ \diagdown \\ N-CO- \\ \diagup \\ R_7 \end{array}$$

wherein
$R_6$ and $R_7$ respectively represent H or $CH_3$.

It is stated that these compounds are useful as broad-spectrum insecticides and may also be used against plant parasitic nematodes.

U.S. Pat. Nos. 3,530,220, 3,658,870 and 3,763,143 disclose and claim a class of alkyl 1-carbamoyl-N-(substituted carbamoyloxy)thioformimidates such as methyl 2-(dimethylamino)-N-[(methylamino)-carbonyloxy]-2-oxoethanimidothioate, $$\begin{array}{c} CH_3 \quad O \quad \quad O \\ \diagdown \quad \| \quad \quad \| \\ N-C-C=N-O-C-NHCH_3. \\ \diagup \quad \quad | \\ CH_3 \quad \quad S-CH_3 \end{array}$$

These compounds are useful in preventing the destructive effects of ticks, mites, insects and nematodes in a variety of applications.

SUMMARY OF THE INVENTION

This invention relates to novel compounds of Formula I, to agriculturally useful compositions containing these compounds as an active ingredient and to a method of using these compounds for controlling plant parasitic nematodes.

$$\begin{array}{c} R_3 \quad O \quad \quad O \\ \diagdown \quad \| \quad \quad \| \\ N-C-N-S-N-COR \\ \diagup \quad \quad | \quad | \\ R_4 \quad \quad R_2 \; R_1 \end{array}$$

(I)

wherein $$R \text{ is } -N=C \diagup^{R_{13}}_{\diagdown SCH_3} \; ;$$

$R_1$ and $R_2$ are the same, and are $C_1$–$C_3$ alkyl;

$R_3$ is H, $C_1$–$C_4$ alkyl, $C_5$–$C_6$ cycloalkyl, $-C(H)_{(2-m)}(CH_3)_m-C\equiv C-R_5$ or $$-C(H)_{(2-m)}(CH_3)_m-C=C \diagup^{R_7}_{\diagdown R_8} \; ;$$
$$\qquad \qquad \qquad \qquad \; | \\ \qquad \qquad \qquad \; R_6$$

$R_4$ is $-C(H)_{(2-n)}(CH_3)_n-C\equiv C-R_9$ or $$-C(H)_{(2-n)}(CH_3)_n-C=C \diagup^{R_{11}}_{\diagdown R_{12}} \; ;$$
$$\qquad \qquad \qquad \qquad \; | \\ \qquad \qquad \qquad \; R_{10}$$

$R_5$, $R_6$, $R_7$, $R_8$, $R_9$, $R_{10}$, $R_{11}$ and $R_{12}$ are independently H or $CH_3$;

$$R_{13} \text{ is } -CH_3 \text{ or } -CN(CH_3)_2; \\ \qquad \qquad \qquad \qquad \; \| \\ \qquad \qquad \qquad \; O$$

m and n are independently 0, 1 or 2; provided that
when $R_3$ is alkenyl and m=1, one or more of $R_6$, $R_7$ and $R_8$ is H; $R_3$ is alkenyl and m=2, two or more of $R_6$, $R_7$ and $R_8$ are H;
when $R_4$ is alkenyl and n=1, one or more of $R_{10}$, $R_{11}$ and $R_{12}$ is H;
when $R_4$ is alkenyl and n=2, two or more of $R_{10}$, $R_{11}$ and $R_{12}$ are H;
further provided that when $R_3$ is $C_5$–$C_6$ cycloalkyl, $-CH(CH_3)_2$, $-CH(CH_3)CH_2CH_3$, or when m is 1, then n is 0 or 1; and when $R_3$ is $-C(CH_3)_3$ or m is 2, then n is 0 (zero).

Preferred for their high activity and/or favorable cost are compounds of Formula I wherein:
(1) $R_1$ and $R_2$ are $-CH_3$;
(2) Those compounds of (1) wherein $R_3$ is H, $C_1$–$C_4$ alkyl or $C_5$–$C_6$ cycloalkyl;
(3) Those compounds of (2) wherein $$R \text{ is } -N=C \diagup^{CN(CH_3)_2}_{\diagdown SCH_3} \; ; \\ \qquad \qquad \qquad \; \| \\ \qquad \qquad \; O$$

(4) Those compounds of (3) wherein $R_3$ is H;
(5) Those compounds of (4) wherein
$R_4$ is $-C(H)_{(2-n)}(CH_3)_nC\equiv CH$ and n is 0, 1 or 2.

Specifically preferred for their excellent activity and/or most favorable cost are the following
2-(dimethylamino)-N-[[N-methyl-N-[N-methyl-N-(2-propynylaminocarbonyl)aminothio]aminocarbonyloxy]]-2-oxoethanimidothioic acid, methyl ester; and
2-(dimethylamino)-N-[[N-[N-(1,1-dimethyl-2-propynylaminocarbonyl)-N-methylaminothio]N-methylaminocarbonyloxy]]-2-oxoethanimidothioic acid, methyl ester.

DETAILED DESCRIPTION OF THE INVENTION

Preparation

Compounds of Formula I may be prepared by reaction of carbamate N-sulfenyl carbamoyl halides of Formula II,

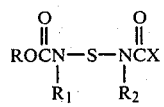
(II)

wherein

X can be F or Cl, with amines of Formula III in the presence of an acid acceptor in a suitable inert solvent (Reaction 1).

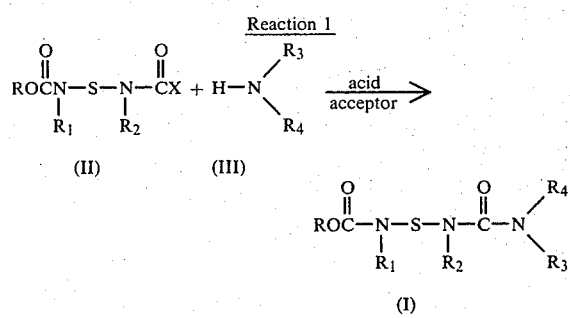

Similarly, the compounds of this invention may be prepared by reaction of the ureidosulfenyl carbamoyl halides of Formula IV

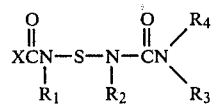

with oximes of Formula V-a in the presence of acid acceptors (Reaction 2),

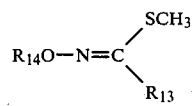

(a) $R_{14}=H$;
(b) $R_{14}=M$, e.g., $Na^+$, $K^+$, or other suitable cation;

or with salts of oximes of Formula V-b in suitable solvents (Reaction 3);

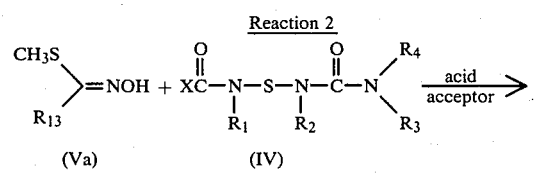

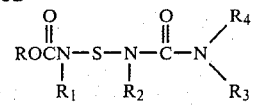

Suitable inert solvents include, but are not limited to, ether, tetrahydrofuran, acetonitrile, methylene chloride, chloroform, carbon tetrachloride, benzene and toluene. Order of addition is not critical. Reaction temperature is not critical, and can vary from, for example, $-20°$ C. to the boiling point of the solvent depending on the reactivity of the components. Ordinarily, the reaction can for convenience be conducted at or near ambient temperature. The acid acceptor should be present in approximately equivalent amounts to the carbamyl halide; however, moderate excess of acid acceptor normally does not present a problem. Intermediates of the types described above are well known in the art. Purification may be accomplished by standard methods, for example, recrystallization or chromatography.

This invention may be further illustrated by the following examples.

EXAMPLE 1

A solution of 0.01 mole (3.26 g) of methyl 2-(dimethylamino)-N-[N-[N-(fluorocarbonyl)-N-methylamino]-N-methylaminocarbonyloxy]-2-oxoethanimidothioate in 13 ml $CH_2Cl_2$ was cooled in an ice-water bath. To this solution was added dropwise a solution of 0.01 mole triethylamine (1.01 g) and 0.01 mole (0.55 g) propargyl amine in 10 ml $CH_2Cl_2$. There was a vigorous exothermic reaction and a precipitate formed. Cooling was removed, and the reaction was stirred overnight at ambient temperature. The reaction mixture was washed twice with water, dried over sodium sulfate, and the solvent was removed leaving 2-(dimethylamino)-N-[[N-methyl-N-[N-methyl-N-(2-propynylaminocarbonyl)-aminothio]carbonyloxy]]-2-oxoethanimidothioic acid, methyl ester, as a very viscous oil.

By the methods discussed, the following comounds can be made:

TABLE 1

$$\underset{R_{13}}{\overset{CH_3S}{\diagdown}}C=N-O-\overset{O}{\underset{\|}{C}}-\underset{R_1}{N}-S-\underset{R_2}{N}-\overset{O}{\underset{\|}{C}}-N\underset{R_3}{\overset{R_4}{\diagup}}$$

| $R_{13}$ | $R_1$ | $R_2$ | $R_3$ | $R_4$ | physical property |
|---|---|---|---|---|---|
| $(CH_3)_2N\overset{O}{\underset{\|}{C}}-$ | $CH_3$ | $CH_3$ | H | $CH_2C\equiv CH$ | viscous oil |

TABLE 1-continued $$\underset{R_{13}}{\overset{CH_3S}{>}}C=N-O-\overset{O}{\underset{\|}{C}}-\underset{R_1}{N}-S-\underset{R_2}{N}-\overset{O}{\underset{\|}{C}}-\underset{R_3}{\overset{R_4}{N}}$$

| $R_{13}$ | $R_1$ | $R_2$ | $R_3$ | $R_4$ | physical property |
|---|---|---|---|---|---|
| $(CH_3)_2N\overset{O}{\underset{\|}{C}}-$ | $CH_3$ | $CH_3$ | H | $C(CH_3)_2C\equiv CH$ | viscous oil |
| $(CH_3)_2N\overset{O}{\underset{\|}{C}}-$ | $C_3H_7$ | $C_3H_7$ | $CH_3$ | $C(CH_3)_2C\equiv CH_3$ | |
| $(CH_3)_2N\overset{O}{\underset{\|}{C}}-$ | $CH_3$ | $CH_3$ | $CH_2-C\equiv CH$ | $C(CH_3)_2-C\equiv CCH_3$ | |
| $(CH_3)_2N\overset{O}{\underset{\|}{C}}-$ | $CH_3$ | $CH_3$ | $CH_2-CH\equiv CH_2$ | $CH_2CH=CH_2$ | |
| $(CH_3)_2N\overset{O}{\underset{\|}{C}}-$ | $C_2H_5$ | $C_2H_5$ | $CH(CH_3)CH=C(CH_3)_2$ | $CH_2CH=CH_2$ | |
| $(CH_3)_2N\overset{O}{\underset{\|}{C}}-$ | $CH_3$ | $CH_3$ | cyclo-$C_6H_{11}$ | $CH_2C\equiv CH$ | |
| $(CH_3)_2N\overset{O}{\underset{\|}{C}}-$ | $CH_3$ | $CH_3$ | $C_4H_9$ | $CH_2CH=C(CH_3)_2$ | |
| $(CH_3)_2N\overset{O}{\underset{\|}{C}}-$ | $CH_3$ | $CH_3$ | $CH_2-C\equiv CH$ | $CH_2C\equiv CH$ | |
| $(CH_3)_2N\overset{O}{\underset{\|}{C}}-$ | $CH_3$ | $CH_3$ | H | $CH_2CH=CH_2$ | |
| $(CH_3)_2N\overset{O}{\underset{\|}{C}}-$ | $CH_3$ | $CH_3$ | H | $CH_2CH=C(CH_3)_2$ | |
| $(CH_3)_2N\overset{O}{\underset{\|}{C}}-$ | $CH_3$ | $CH_3$ | cyclo-$C_5H_9$ | $CH_2CH=CH_2$ | |
| $CH_3$ | $CH_3$ | $CH_3$ | $CH_3$ | $CH_2C\equiv CH$ | glassy solid |
| $CH_3$ | $CH_3$ | $CH_3$ | H | $CH_2C\equiv CH$ | mp 94–98° C. |
| $CH_3$ | $CH_3$ | $CH_3$ | H | $CH_2CH=CH_2$ | mp 66–69° C. |
| $CH_3$ | $CH_3$ | $CH_3$ | H | $C(CH_3)_2C\equiv CH$ | viscous oil |
| $CH_3$ | $CH_3$ | $CH_3$ | $CH_2CH=CH_2$ | $CH_2CH=CH_2$ | |
| $CH_3$ | $CH_3$ | $CH_3$ | $CH_2C\equiv CH$ | $CH_2C\equiv CH$ | |
| $(CH_3)_2N\overset{O}{\underset{\|}{C}}-$ | $CH_3$ | $CH_3$ | $-C(CH_3)_2C\equiv CH$ | $-CH_2C\equiv CH$ | |
| $(CH_3)_2N\overset{O}{\underset{\|}{C}}-$ | $CH_3$ | $CH_3$ | $-CH(CH_3)_2$ | $-CH_2CH=CH_2$ | |
| $(CH_3)_2N\overset{O}{\underset{\|}{C}}-$ | $CH_3$ | $CH_3$ | $-\underset{CH_3}{\overset{\|}{C}H}CH_2CH_3$ | $-CH_2CH=CH_2$ | |
| $(CH_3)_2N\overset{O}{\underset{\|}{C}}-$ | $CH_3$ | $CH_3$ | $-CH(CH_3)C\equiv H$ | $-CH(CH_3)C\equiv CH$ | |
| $(CH_3)_2N\overset{O}{\underset{\|}{C}}-$ | $CH_3$ | $CH_3$ | $-C(CH_3)_3$ | $-CH_2C\equiv CH$ | |
| $(CH_3)_2N\overset{O}{\underset{\|}{C}}-$ | $CH_3$ | $CH_3$ | -cyclo-$C_6H_{11}$ | $-CH_2CH=CH_2$ | |
| $(CH_3)_2N\overset{O}{\underset{\|}{C}}-$ | $CH_3$ | $CH_3$ | -cyclo-$C_6H_{11}$ | $-CH(CH_3)C\equiv CH$ | |
| $(CH_3)_2N\overset{O}{\underset{\|}{C}}-$ | $CH_3$ | $CH_3$ | -cyclo-$C_6H_{11}$ | $-CH(CH_3)CH=CH_2$ | |
| $(CH_3)_2N\overset{O}{\underset{\|}{C}}-$ | $CH_3$ | $CH_3$ | $-CH_2CH(CH_3)_2$ | $-C(CH_3)_2C(CH_3)=CH_2$ | |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b)

about 1% to 99.9% solid or liquid inert diluent(s). More specifically, they will contain these ingredients in the approximate proportions set forth in the following table.

TABLE 2

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Solutions Emulsions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers," 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions can be prepared by simply mixing the ingredients. Fine solid compositions can be made by blending, and usually grinding, as in a hammer or fluid energy mill. Suspensions may be prepared by wet milling (see, for example, Littler, U.S. Pat. No. 3,060,084). Granules and pellets can be made by spraying the active material on preformed granular carriers or by agglomeration techniques. See J. E. Browning, "Agglomeration," *Chemical Engineering*, Dec. 4, 1967, pp. 147ff. and "Perry's Chemical Engineer's Handbook," 4th Ed., McGraw-Hill, New York, 1963, pp. 8-59ff.

This invention is further illustrated in the following examples in which all parts are by weight.

EXAMPLE 2

| Wettable Powder | |
|---|---|
| 2-(dimethylamino)-N-[[N-methyl-N-[N-methyl-N-(2-propynyl-aminocarbonyl)aminothio]amino-carbonyloxy]]-2-oxoethan-imidothioic acid, methyl ester | 50% |
| Sodium alkylnaphthalenesulfonate | 2% |
| Low viscosity methyl cellulose | 2% |

| -continued | |
|---|---|
| Wettable Powder | |
| Diatomaceous earth | 46% |

The ingredients are blended, coarsely hammer-milled and then air milled to produce particles of active essentially all below 10 microns in diameter. The product is reblended before packaging.

EXAMPLE 3

| Solution | |
|---|---|
| 2-(Dimethylamino)-N-[[N-methyl-N-[N-methyl-N-(2-propynylamino-carbonyl)aminothio]aminocarbonyl-oxy]]-2-oxoethanimidothioic acid, methyl ester | 30% |
| N-methylpyrrolidone | 70% |

The ingredients are combined and stirred to produce a solution, which can be used for low volume applications.

EXAMPLE 4

| Solution | |
|---|---|
| 2-(Dimethylamino)-N-[[N-[N-(1,1-dimethyl-2-propynylaminocarbonyl)-N-methylaminothio]-N-methylamino-carbonyloxy]]-2-oxoethanimido-thioic acid, methyl ester | 20% |
| Isophorone | 80% |

The ingredients are combined and stirred to produce a solution suitable for direct, low volume application.

EXAMPLE 5

| Granule | |
|---|---|
| Wettable Powder of Example 2 | 10% |
| Attapulgite granules (U.S.S. No. 20-40; 0.84-0.42 mm) | 90% |

A slurry of wettable powder containing 50% solids is sprayed on the surface of attapulgite granules in a double-cone blender. The granules are then dried and packaged.

EXAMPLE 6

| Granule | |
|---|---|
| Wettable powder of Example 2 | 15% |
| Gypsum | 69% |
| Potassium sulfate | 16% |

The ingredients are blended in a rotating mixer with a water spray to accomplish granulation. When most of the material has reached the desired range of 1.0 to 0.42 mm (U.S.S. No. 18 to 40 sieves), the granules are removed, dried, and screened. Oversize material is crushed to produce additional material in the desired range. These granules contain about 7.5% active ingredient.

EXAMPLE 7

| Extruded Pellet | |
|---|---|
| 2-(Dimethylamino)-N-[[N-methyl-N-[N-methyl-N-(2-propynyl-aminocarbonyl)aminothio]aminocarbonyloxy]]-2-oxoethanimidothioic acid, methyl ester | 25% |
| Anhydrous sodium sulfate | 10% |
| Crude calcium ligninsulfonate | 5% |
| sodium alkylnaphthalenesulfonate | 1% |
| Calcium/magnesium bentonite | 59% |

The ingredients are blended, hammer milled and then moistened with about 12% water. The mixture is extruded into cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

| High Strength Concentrate | |
|---|---|
| 2-(Dimethylamino)-N-[[N-methyl-N-[N-methyl-N-(2-propynylaminocarbonyl)aminothio]aminocarbonyloxy]]-2-oxoethanimidothioic acid, methyl ester | 98.5% |
| Silica aerogel | 0.5% |
| Synthetic amorphous fine silica | 1.0% |

The ingredients are blended and ground in a hammer mill to produce a high strength concentrate practically all particles of which pass a U.S.S. No. 50 sieve (0.3 mm openings). This material may then be formulated in a variety of ways.

EXAMPLE 9

| Dust | |
|---|---|
| Wettable powder of Example 2 | 10% |
| Pyrophyllite (powder) | 90% |

The wettable powder and the pyrophyllite diluent are thoroughly blended and then packaged. The product is suitable for use as a dust.

UTILITY

The compounds of Formula (I) are well suited to the control of plant-parasitic nematodes inhabiting soil in which the plants are planted or are to be planted. The physical characteristics of the compounds of Formula (I) permit them to be placed readily at the site of nematode presence or activity without disturbing already established plants. The physical nature of the compounds of Formula (I) permit their movement deep into undisturbed soil around plant roots, often the site of nematode attack. The safety margin for plants make practical such application as well as application to soil being prepared for planting and application directly to seeds and growing plants at rates well above those required to control the nematodes.

Use rates for application to soil in which plants are growing are generally the same as those for application to soil being prepared for planting. Such rates range from about 0.125 to 100 kilograms of active ingredient per hectare of surface actually treated. Rates of 0.25 to 50 kilograms per hectare are most preferred for these uses for reasons of convenience and economy.

Other methods of applying the compounds of Formula (I) to prevent the destructive effects of plant-parasitic nematodes include: spraying above-ground parts such as stems, leaves or buds in which nematodes are already present or where later attack is possible; dipping or soaking reproductive parts such as seeds, potato, and cane pieces, slips (i.e., pineapple) or bulbs (which are already infested or are to be planted in infested soil) in a water suspension, solution or emulsion of the active ingredient; or immersing the root system or the entire plant of nursery stock or transplants in a water system to disinfect them or provide protection against subsequent invasion. The rates of active ingredient in the sprays or dips used as noted just preceding are 12 grams to 4.8 kilograms per 100 liters of water. Preferred rates are in the range of 30 grams to 1.2 kilograms per 100 liters.

PESTS CONTROLLED

Representative nematodes from which the compounds of Formula (I) offer protection are the following:

Awl nematode—*Dolichodorus heterocephalus*
Banana nematode—*Pratylenchus musicola*
Bud and leaf nematode—*Aphelenchoides spp.*
Burrowing nematode—*Radopholus similis*
Carrot root nematode—*Heterodera carotae*
Coffee root-knot nematode—*Meloidogyne exigua*
Corn nematode—*Pratylenchus zeae*
Dagger nematodes—*Xiphinema spp.*
Golden nematode—*Globodera rostochiensis*
Grass nematode—*Anguina agrostis*
Lance nematodes—*Hoplolaimus spp.*
Lesion nematodes—*Pratylenchus spp.*
Northern root-knot nematode—*Meloidogyne hapla*
Pea root nematode—*Heterodera goettingiana*
Peanut root-knot nematode—*Meloidogyne arenaria*
Pin nematodes—*Paratylenchus spp.*
Potato rot nematode—*Ditylenchus destructor*
Reniform nematode—*Rotylenchulus reniformis*
Rice nematode—*Ditylenchus angustus*
Ring nematodes—*Criconemoides spp.*
Smooth-headed lesion nematode—*Pratylenchus brachyurus*
Southern root-knot nematode—*Meloidogyne incognita*
Soybean cyst nematode—*Heterodera glycines*
Spiral nematodes—*Helicotylenchus spp.*
Stem and bulb nematode—*Ditylenchus dipsaci*
Sting nematodes—*Belonolaimus spp.*
Stubby-root nematodes—*Trichodorus spp.*
Sugar beet nematode—*Heterodera schachtii*
Tobacco cyst nematode—*Heterodera tabacum*
Tobacco stunt nematode—*Tylenchorhynchus claytoni*
Wheat nematode—*Anguina tritici.*

APPLICATION

In applying the compounds of Formula (I) for pest control, the compound is of course applied in an amount sufficient to exert the desired pesticidal action. The amounts required to give pest control action however, are governed by such variables as temperature, time of the year, moisture, type of application, pest species to be controlled and the like. Thus, it is not possible to state any one method or rate of application which would be generally satisfactory. It is possible however to describe generally some of the various methods and rates of application for certain areas of use and to which the compounds of Formula (I) are best suited.

Thus, the compounds of Formula (I) wherein

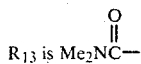

can be used to control plant parasitic nematodes by distributing the chemical evenly over the surface of plants which are infested or which are to be protected from subsequent root infestation. Thus foliar application of these compounds is sufficient to protect plant roots. Due to the margin of safety for plants and animals characteristic of the compounds of Formula (I), such applications can be made without danger to the applicator or fear of damage to the plant when used as directed. Use rates for this type of application are in the range of 0.05 to 34 kilograms of active ingredient per hectare and rates of 0.2 to 8 kilograms per hectare are most preferred for reasons of convenience and economy. This type of application may need to be repeated at intervals of approximately 20 days. Such applications can be made with any of a variety of widely-available types of equipment ordinarily used for such applications.

MODIFIERS

Additional modifiers can be used to advantage in the composition of this invention. Thus, although the compounds of Formula (I) are quite stable under most conditions, the use of a desiccant, buffering agent or materials such as urea, which inactivate catalytic sites on diluent particles, can prove desirable. Additives which will inhibit corrosion, reduce foam, reduce caking and increase flocculation can also be used. In addition, bactericides, fungicides, bacteriostats and fungistats and other insecticides, acaricides and nematicides are often desirably present in the compositions of this invention in amounts of 0.025 to 10 parts by weight for each 1 part by weight of compound of Formula (I). Suitable biologically active compounds are well known to those skilled in the art.

Fungicides and fungistats with which compounds of Formula (I) are preferably combined include pentachloronitrobenzene (PCNB); thiram; dodine; maneb; 1,4-dichloro-2,5-dimethoxybenzene; dimethyl ester of 2-carboxyamino-1-benzimidazolecarboxylic acid; N-trichloromethylthiotetrahydrophthalimide; N-trichloromethylthiophthalimide; sodium and calcium propionate; and 3,3'-ethylene-bis(tetrahydro-4,6-dimethyl-2H-1,3,5-thiadiazine-2-thione).

The nematicidal properties of compounds in Formula (I) are demonstrated in the following greenhouse tests:

TEST A—SOIL TEST

Pots containing soil infested with the Southern root-knot nematode (*Meloidogyne incognita*) were treated with 2-(dimethylamino)-N-((N-methyl-N-[N-methyl-N-(2-propynylaminocarbonyl)aminothio]aminocarbonyloxy]-2-oxoethanimidothioic acid, methyl ester at 0.5 and 0.25 kg/ha by mixing in the soil. Untreated infested soil was included for comparison. Cucumber seeds were planted and grown in treated and untreated soil under normal greenhouse conditions. After two weeks, the roots were examined for nematode attack and the following observations on nematode control were recorded:

TABLE 3

| Treatment | kg/ha | % Root-Knot Nematode Control |
|---|---|---|
| 2-(dimethylamino)-N-[[N-methyl-N-[N-methyl-N-(2-propynylaminocarbonyl)aminothio]aminocarbonyloxy]]-2-oxoethanimidothioic acid, methyl ester | 0.5 | 100 |
| 2-(dimethylamino)-N-[[N-methyl-N-[N-methyl-N-(2-propynylaminocarbonyl)aminothio]aminocarbonyloxy]]-2-oxoethanimidothioic acid, methyl ester | 0.25 | 100 |
| Untreated | — | 0 |

TEST B—DOWNWARD TRANSLOCATION TEST

Tomato plants 12 inches high growing in 5-inch pots were treated by spraying the foliage to run off with 2-(dimethylamino)-N-((N-methyl-N-[N-methyl-N-(2-propynylaminocarbonyl)aminothio]aminocarbonyloxy))-2-oxoethanimidothioic acid, methyl ester at the rates of 2 kg/833 liters. Prior to spraying, the soil surface was covered to insure that no chemical dripped onto the soil. Twenty-four hours after treatment, the covering was removed and root-knot nematode eggs and larvae were inoculated onto the soil surface and watered in. Care was taken throughout the experiment to insure that chemical on the leaves did not come in contact with the soil. Three weeks after treatment, the roots were examined for nematode control and the following observations noted:

TABLE 4

| Treatment | kg/833 l. Sprayed to Run Off | % Root-Knot Nematode Control |
|---|---|---|
| 2-(dimethylamino)-N-[[N-methyl-N-[N-methyl-N-(2-propynylaminocarbonyl)aminothio]aminocarbonyloxy]]-2-oxoethanimidothioic acid, methyl ester | 2 | 73% |
| Control (untreated) | — | 0 |

What is claimed is:

1. A compound of the formula

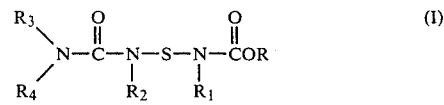

wherein

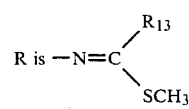

$R_1$ and $R_2$ are the same and are $C_1$–$C_3$ alkyl;
$R_3$ is H, $C_1$–$C_4$ alkyl, $C_5$–$C_6$ cycloalkyl, $-C(H)_{(2-m)}(CH_3)_m-C{\equiv}C-R_5$ or $$-C(H)_{(2-m)}(CH_3)_m-C=C\begin{smallmatrix}R_7\\ \\R_8\end{smallmatrix}\ ;$$
$$\quad\quad\quad\quad\quad\quad\quad\quad R_6$$

R₄ is $-C(H)_{(2-n)}(CH_3)_n-C\equiv C-R_9$ or $$-C(H)_{(2-n)}(CH_3)_n-C=C\begin{smallmatrix}R_{11}\\ \\R_{12}\end{smallmatrix}\ ;$$
$$\quad\quad\quad\quad\quad\quad\quad\quad R_{10}$$

$R_5$, $R_6$, $R_7$, $R_8$, $R_9$, $R_{10}$, $R_{11}$ and $R_{12}$ are independently H or $CH_3$;

$$R_{13} \text{ is } -CH_3 \quad \text{or} \quad -\overset{\overset{O}{\|}}{C}N(CH_3)_2$$

m and n are independently 0, 1 or 2; provided that
when $R_3$ is alkenyl and m=1, one or more of $R_6$, $R_7$ and $R_8$ is H;
when $R_3$ is alkenyl and m=2, two or more of $R_6$, $R_7$ and $R_8$ are H;
when $R_4$ is alkenyl and n=1, one or more of $R_{10}$, $R_{11}$ and $R_{12}$ are H;
when $R_4$ is alkenyl and n=2, two or more of $R_{10}$, $R_{11}$ and $R_{12}$ are H;
further provided that when $R_3$ is $C_5$—$C_6$ cycloalkyl, $-CH(CH_3)_2$, $-CH(CH_3)CH_2CH_3$, or when m is 1, then n is 0 or 1; and when $R_3$ is $-C(CH_3)_3$ or m is 2, then n is 0 (zero).

2. A compound of claim 1 in which $R_1$ and $R_2$ are $-CH_3$.

3. A compound of claim 2 in which $R_3$ is H, $C_1$-$C_4$ alkyl or $C_5$-$C_6$ cycloalkyl.

4. A compound of claim 3 in which $$R \text{ is } -N=C\begin{smallmatrix}\overset{O}{\|}\\CN(CH_3)_2\\ \\SCH_3\end{smallmatrix}$$

5. A compound of claim 4 in which $R_3$ is H.

6. A compound of claim 5 in which $R_4$ is $-C(H)_{(2-n)}(CH_3)_nC\equiv CH$ and n is 0, 1 or 2.

7. A compound of claim 1 which is 2-(dimethylamino)-N-[[N-methyl-N-[N-methyl-N-(2-propynylaminocarbonyl)aminothio]aminocarbonyloxy]]-2-oxoethanimidothioic acid, methyl ester.

8. A compound of claim 1 which is 2-(dimethylamino)-N-[[N-[N-(1,1-dimethyl-2-propynylaminocarbonyl)-N-methylaminothio]-N-methylaminocarbonyloxy]]-2-oxoethanimidothioic acid, methyl ester.

9. A composition for controlling plant parasitic nematodes consisting essentially of an effective amount of a compound of claim 1 and at least one of (a) about 0.1% to 20% by weight surfactant(s) and (b) about 1% to 99.9% by weight solid or liquid diluent(s).

10. A composition for controlling plant parasitic nematodes consisting essentially of an effective amount of a compound of claim 2 and at least one of (a) about 0.1% to 20% by weight surfactant(s) and (b) about 1% to 99.9% by weight solid or liquid diluent(s).

11. A composition for controlling plant parasitic nematodes consisting essentially of an effective amount of a compound of claim 3 and at least one of (a) about 0.1% to 20% by weight surfactant(s) and (b) about 1% to 99.9% by weight solid or liquid diluent(s).

12. A composition for controlling plant parasitic nematodes consisting essentially of an effective amount of a compound of claim 4 and at least one of (a) about 0.1% to 20% by weight surfactant(s) and (b) about 1% to 99.9% by weight solid or liquid diluent(s).

13. A composition for controlling plant parasitic nematodes consisting essentially of an effective amount of a compound of claim 5 and at least one of (a) about 0.1% to 20% by weight surfactant(s) and (b) about 1% to 99.9% by weight solid or liquid diluent(s).

14. A composition for controlling plant parasitic nematodes consisting essentially of an effective amount of a compound of claim 6 and at least one of (a) about 0.1% to 20% by weight surfactant(s) and (b) about 1% to 99.9% by weight solid or liquid diluent(s).

15. A composition for controlling plant parasitic nematodes consisting essentially of an effective amount of the compound of claim 7 and at least one of (a) about 0.1% to 20% by weight surfactant(s) and (b) about 1% to 99.9% by weight solid or liquid diluent(s).

16. A composition for controlling plant parasitic nematodes consisting essentially of an effective amount of the compound of claim 8 and at least one of (a) about 0.1% to 20% by weight surfactant(s) and (b) about 1% to 99.9% by weight solid or liquid diluent(s).

17. A method of controlling plant-parasitic nematodes which comprises applying to the locus to be protected an effective amount of a compound of claim 1.

18. A method of controlling plant-parasitic nematodes which comprises applying to the locus to be protected an effective amount of a compound of claim 2.

19. A method of controlling plant-parasitic nematodes which comprises applying to the locus to be protected an effective amount of a compound of claim 3.

20. A method of controlling plant-parasitic nematodes which comprises applying to the locus to be protected an effective amount of a compound of claim 4.

21. A method of controlling plant-parasitic nematodes which comprises applying to the locus to be protected an effective amount of a compound of claim 5.

22. A method of controlling plant-parasitic nematodes which comprises applying to the locus to be protected an effective amount of a compound of claim 6.

23. A method of controlling plant-parasitic nematodes which comprises applying to the locus to be protected an effective amount of the compound of claim 7.

24. A method of controlling plant-parasitic nematodes which comprises applying to the locus to be protected an effective amount of the compound of claim 8.

* * * * *